(12) United States Patent  (10) Patent No.: US 10,166,103 B2
Ozaki  (45) Date of Patent: Jan. 1, 2019

(54) VALVE CUSP SIZER

(71) Applicant: JAPANESE ORGANIZATION FOR MEDICAL DEVICE DEVELOPMENT, INC., Tokyo (JP)

(72) Inventor: Shigeyuki Ozaki, Tokyo (JP)

(73) Assignee: Japanese Organization For Medical Device Development, Inc., Tokyo (JP)

(*) Notice: Subject to any disclaimer, the term of this patent is extended or adjusted under 35 U.S.C. 154(b) by 168 days.

(21) Appl. No.: 15/509,195

(22) PCT Filed: Aug. 19, 2015

(86) PCT No.: PCT/JP2015/073197
§ 371 (c)(1),
(2) Date: Mar. 7, 2017

(87) PCT Pub. No.: WO2016/039095
PCT Pub. Date: Mar. 17, 2016

(65) Prior Publication Data
US 2017/0281347 A1  Oct. 5, 2017

(30) Foreign Application Priority Data
Sep. 8, 2014  (JP) ................................ 2014-182150

(51) Int. Cl.
*A61B 5/107*  (2006.01)
*A61F 2/24*  (2006.01)
*A61F 2/76*  (2006.01)

(52) U.S. Cl.
CPC .......... *A61F 2/2496* (2013.01); *A61B 5/1076* (2013.01); *A61F 2/2412* (2013.01);
(Continued)

(58) Field of Classification Search
CPC ............................... A61B 5/107; A61B 5/1076
(Continued)

(56) References Cited

U.S. PATENT DOCUMENTS

2006/0265053 A1* 11/2006 Hunt ..................... A61F 2/2412
623/1.24
2010/0217092 A1  8/2010 Paolitto
(Continued)

FOREIGN PATENT DOCUMENTS

JP  2009-505785 A  2/2009
JP  2009-077838 A  4/2009
JP    5106019 B2  12/2012

OTHER PUBLICATIONS

International Search Report of International Application No. PCT/JP2015/073197 completed Oct. 21, 2015 and dated Nov. 2, 2015 (2 pages).
(Continued)

*Primary Examiner* — G. Bradley Bennett
(74) *Attorney, Agent, or Firm* — Pyprus Pte Ltd (57) ABSTRACT

To provide a valve cusp sizer which is small and easy to handle. The present invention relates to a valve cusp sizer 100 for determining the size of a valve cusp depending on the size of a cardiac valve. The valve cusp sizer 100 includes a front surface 10 formed in an arcuate surface form to be abutted against an organism, a back surface 20 positioned on an opposite surface side of the front surface 10, and a pinching portion 30 protruding from the back surface 20. By removing a grip member and a grip member attachment portion from a conventional valve cusp sizer in this manner, and by forming the pinching portion 30 to be held by a clamp, tweezers, or the like, it is possible to dramatically miniaturize the valve cusp sizer while maintaining necessary functions of the valve cusp sizer.

7 Claims, 8 Drawing Sheets

(52) U.S. Cl.
CPC .............. *A61F 2/2463* (2013.01); *A61F 2/76* (2013.01); *A61F 2/2442* (2013.01)

(58) Field of Classification Search
USPC .......................................................... 33/512
See application file for complete search history.

(56) References Cited

U.S. PATENT DOCUMENTS

| | | | | |
|---|---|---|---|---|
| 2010/0331971 | A1* | 12/2010 | Keranen | ............... A61F 2/2445 623/2.11 |
| 2011/0251598 | A1 | 10/2011 | Ozaki | |
| 2017/0189173 | A1* | 7/2017 | Ozaki | ................... A61F 2/2415 |
| 2017/0304052 | A1* | 10/2017 | Ozaki | ....................... A61F 2/24 |
| 2018/0153690 | A1* | 6/2018 | Spence | ................. A61F 2/0077 |
| 2018/0296162 | A1* | 10/2018 | Kassab | ................ A61B 5/6853 |

OTHER PUBLICATIONS

Shigeyuki Ozaki: Aortic valvuloplasty using autologous pericardium. Jinko Zoki 39(3): 157-161, 2010.
1st Office Action of Chinese patent application No. 2015800312379 dated Oct. 30, 2017 (2 pages).

\* cited by examiner

VALVE CUSP SIZER

TECHNICAL FIELD

The present invention relates to a valve cusp sizer for measuring the size of a valve cusp composing a cardiac valve. The valve cusp sizer is used for forming a valve cusp material of the cardiac valve from an artificial membrane or a biomembrane, for example, during an aortic valvuloplasty or an aortic valve reconstructive operation.

BACKGROUND ART

A heart works as a pump that sends a blood to the whole body by way of an aorta. For example, a cardiac valve (aortic valve), that is formed at the exit where the blood flows out from a left ventricle to the aorta, is composed of cup-shaped three valve cusps of a thin membrane. In a state that a fluid pressure of a blood flow is low, inner membranes of the valve cusps are joined to each other to close the cardiac valve, thereby blocking the blood flow. Whereas, when the fluid pressure of the blood flow is increased, the inner membranes of the valve cusps are spaced apart from each other to open the cardiac valve, thereby allowing the blood to flow from the heart into the aorta. Each of the valve cusps has commissure portions corresponding to a left end and a right end thereof, and each of the valve cusps is integrated with an inner wall of the aorta at the commissure portions.

When arteriosclerosis, etc. proceed along with aging, calcium is deposited to the valve cusps and thereby calcifying and hardening the valve cusps. This phenomenon causes a disease of an aortic valve stenosis in which the movement of the valve cusps is restricted and the valve cusps open insufficiently. As a result, the left ventricle wall becomes thicker to be enlarged. When the thickness of a wall of the cardiac muscle is excessively increased, nutrition and oxygen delivered by the blood flow supplied from the coronary arteries are insufficient. This results in a myocardial ischemia (a state of insufficient nutrition and oxygen) of the heart. Particularly, if the myocardial ischemia is caused when the oxygen demand is increased, for example, during activity, it may possibly cause symptoms such as chest pain and syncope.

As a result of an earnest study, the present inventor has established an aortic valvuloplasty, instead of a conventional valve replacement, as therapeutics for such a disease. The aortic valvuloplasty is a technique as follows. That is, among the valve cusps hardened due to deposition of calcium, valve cusps that can be used by decalcification are left as much as possible, and only valve cusps that cannot be used are excised to be repaired by replacing the excised valve cusps with another aortic valve formed of autologous biomembrane, etc. In this case, since the valve cusps are formed by an autologous pericardium to be used as a new aortic valve, there is no problem of causing rejection or blood clotting reaction (thrombus) and purchasing an expensive prosthetic valve is not required. In the aortic valvuloplasty, a new valve cusp conforming to the diameter of a patient's aorta is required to be cutout from a planar pericardium. However, there has been a problem how to determine the size of the new valve cusp conforming to the diameter of the patient's aorta.

Figure 8:
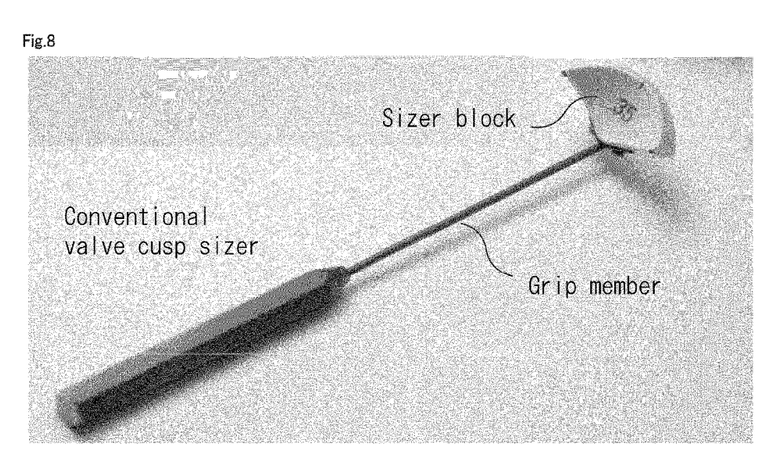
FIG. 8 is a photograph showing a conventional valve cusp sizer.

Therefore, the inventor of the present invention developed a valve cusp forming instrument for measuring the size of a patient's valve cusp accurately and forming a valve cusp conforming to the diameter of the patient's aorta (see Patent Document 1). Patent Document 1 discloses a valve cusp forming instrument for using in the aortic valvuloplasty. The valve cusp forming instrument includes a plurality of valve cusp sizers and templates. An example of valve cusp sizer is shown in FIG. 2 of Patent Document 1. A photograph of an actual valve cusp sizer is shown in FIG. 8 of the present application. As shown in FIG. 8 and the like, the conventional valve cusp sizer has a sizer block and a grip member attached to the sizer block. The sizer block has an arcuate surface formed by cutting a column at an angle conforming to the central angle for the commissure portions of the valve cusp. The sizer block is also provided with contact probe portions for positioning both ends of the arcuate surface to the commissure portions of the valve cusp. In the valve cusp forming instrument disclosed in Patent Document 1, each of a plurality of differently-sized sizer blocks are connected to a plurality of grip members to be gripped by hands, as shown in FIG. 1 of Patent Document 1.

The aortic valvuloplasty is disclosed in Shigeyuki OZAKI "Jiko Shinmaku Wo Shiyou Shita Daidoumyakuben Keiseijutsu [Aortic valvuloplasty using autologous pericardium]" *Jinko Zoki,* Vol. 39 (2010), No. 3, 157-161. (see Non-Patent Literature 1 below.) Non-Patent Literature 1 discloses a valve cusp sizer including a sizer block and a grip member as described above (see FIG. 2 of Non-Patent Literature 1).

PRECEDING TECHNICAL DOCUMENT

Patent Document:
Patent Document 1: Japanese Patent No. 5106019.
Non-Patent Literature:
Non-Patent Literature 1: Shigeyuki OZAKI "Jiko Shinmaku Wo Shiyou Shita Daidoumyakuben Keiseijutsu [Aortic valvuloplasty using autologous pericardium]" *Jinko Zoki,* Vol. 39 (2010), No. 3, 157-161.

SUMMARY OF THE INVENTION

Technical Problem

The conventional valve cusp sizer, however, has such a structure that the grip member is attached to each of the differently-sized sizer blocks. This structure makes the entire size of the conventional valve cusp sizer large and makes it hard to handle the conventional valve cusp sizer. That is, as shown in FIG. 8 of the present invention, a long-extended grip member is necessary for the conventional valve cusp sizer, and an attachment portion for the grip member is necessary to be reserved in a sizer head. Accordingly, it is difficult to insert the sizer head of the conventional valve cusp sizer into a base of the narrow aorta. Further, it is necessary to take care not to injure a vessel wall by contacting the sizer head with the vessel wall.

In addition, since the conventional valve cusp sizer has the structure that the grip member is attached to each of the differently-sized sizer blocks, the capacity of a container in which a plurality of types of valve cusp sizers are accommodated becomes large as shown in, for example, FIG. 1 of Patent Document 1. In a case that the container is too large, it is difficult to keep the container at an operator's hand. Therefore, the plurality of types of valve cusp sizers are kept at a place far from an operation field, and a delivery of the valve cusp sizers is needed between the operator and an assistant each time when another size of valve cusp sizer is needed. Such a delivery of the valve cusp sizers results in a loss of operative time.

Accordingly, at the present time, a valve cusp sizer which is small and easy to handle is required.

Solution to Problem

The inventor of the present invention diligently studied solutions for the above described problems of the conventional invention and obtained the following knowledge. That is, by removing a grip member and a grip member attachment portion from a conventional valve cusp sizer, and by forming a pinching portion to be held by a clamp, tweezers, or the like, it is possible to dramatically miniaturize the valve cusp sizer while maintaining necessary functions of the valve cusp sizer. The present inventor thought that the problems of the prior arts would be solved based on such knowledge, and completed the present invention. Specifically, the present invention has a structure described below.

The present invention relates to a valve cusp sizer. The valve cusp sizer is a surgical instrument used for determining (measuring) the size of a valve cusp conforming to the size of a cardiac valve.

The valve cusp sizer of the present invention includes a front surface 10 having an arcuate surface form to be abutted against an organism, a back surface 20 positioned on an opposite surface side of the front surface 10, and a pinching portion 30 protruding from the back surface 20. The front surface 10 is formed in the arcuate surface form so that a central part between left and right ends thereof projects toward a side of the organism. The pinching portion 30 is formed in a shape to be pinched by a surgical instrument. For example, if the pinching portion 30 is formed in a shape having flat surfaces at left and right sides thereof, the pinching portion 30 can be pinched by the surgical instrument.

Since the valve cusp sizer has the above described structure in which the pinching portion 30 is provided on the back surface 20 thereof, the pinching portion 30 can be pinched by a clamp or tweezers. This structure makes it unnecessary for the valve cusp sizer to be provided with a grip member to be gripped by hands. This grip member is a member occupying the most part of the structure in the conventional valve cusp sizer. Since the grip member may be omitted, the valve cusp sizer of the present invention can be miniaturized dramatically. The valve cusp sizer miniaturized in this manner can be inserted easily into the base of the narrow aorta. Further, a risk of injuring the organism by contacting the valve cusp sizer with the vessel wall of the aorta can be reduced. Moreover, since the valve cusp sizer is miniaturized, a plurality of types (for example, 9 types) of differently-sized valve cusp sizers can be accommodated in a small container. This makes it possible to keep a set of the valve cusp sizers around the operator's hand during an operation such as aortic valvuloplasty, and results in shortening an operative time.

In the valve cusp sizer of the present invention, the front surface 10 may preferably have left and right contact probe portions 11, 12 at the left and right ends thereof to be contacted with left and right commissure portions of the valve cusp.

The above described structure, in which the contact probe portions 11, 12 are provided on the front surface 10, makes it possible to determine (measure) the size of the patient's valve cusp more appropriately.

In the valve cusp sizer of the present invention, the back surface 20 may preferably be formed in a shape projecting toward the same direction as the front surface 10 (for example, an arcuate surface form).

The above described structure, in which the back surface 20 is formed in the shape projecting toward the same direction as the front surface 10, further miniaturizes the valve cusp sizer. That is, since an attachment portion of a grip member is necessary for the conventional valve cusp sizer (see FIG. 8) to be provided on the back surface 20 thereof, the back surface 20 projects toward a direction opposite to the front surface 10. However, such a shape makes a head portion of the valve cusp sizer large and difficult to be inserted into the narrow aorta. Therefore, in the valve cusp sizer of the present invention, the attachment portion of the grip member has been removed from the back surface 20, and the back surface 20 has been formed in the shape projecting toward the same direction as the front surface 10 (for example, an arcuate surface form). This structure makes it easy to insert the valve cusp sizer into a narrow portion of the organism.

In the valve cusp sizer of the present invention, the pinching portion 30 may preferably be formed to have a length by which the pinching portion 30 does not protrude beyond left and right back ends 21, 22 of the back surface 20.

By defining the length of the pinching portion 30 not to exceed a certain length as the above described structure, the valve cusp sizer can be adjusted in an appropriate size. Namely, by adjusting the length of the pinching portion 30 so that the pinching portion 30 does not protrude beyond the back ends 21, 22 of the back surface 20, it is possible to prevent the pinching portion 30 from touching the vessel wall and from interfering an insertion of the valve cusp sizer into the aorta.

In the valve cusp sizer of the present invention, at least left and right side surfaces 31, 32 of the pinching portion 30 may preferably be formed by a slip stopper 71, or a nonslip treatment 72 may preferably be applied to the at least left and right side surfaces 31, 32 of the pinching portion 30.

By making efforts to prevent slipping for the pinching portion 30 as the above described structure, the pinching portion 30 can be pinched by a clamp or tweezers easily.

In the valve cusp sizer of the present invention, at least a part of the pinching portion 30 may preferably be inclined upwardly. An inclined state of the pinching portion 30 includes a state that the pinching portion 30 stands perpendicular to a placing surface on which the valve cusp sizer is placed.

The valve cusp sizer of the present invention has a structure to be held from upside by an operator via a clamp or the like. Therefore, if a part of the pinching portion 30 is inclined upwardly as described above, the operator can easily pinch the pinching portion 30. Further, if a part of the pinching portion 30 is inclined upwardly, it is possible to pinch the pinching portion 30 by a surgical instrument such as Kelly clamp in a state that a grip member of the surgical instrument is parallel to the inclination depending on the inclination angle. As a result, the valve cusp sizer is abutted against the commissure portions at an appropriate angle, thereby reducing a measurement error.

Preferably, the valve cusp sizer of the present invention may not be provided with a grip member (see FIG. 8) extending upwardly beyond the contact probe portions 11, 12 to be held by hands.

Effect of the Invention

According to the present invention, a valve cusp sizer which is small and easy to handle can be provided.

DESCRIPTION OF EMBODIMENTS

An explanation of an embodiment of the present invention will be made below with reference to the drawings. The present invention, however, is not limited to the embodiment explained below, and includes modifications appropriately modified by a person skilled in the art in a range obvious from the embodiment explained below.

Note that, in the specification of the present application, "A to B" means "not less than A and not more than B".

Figure 1:
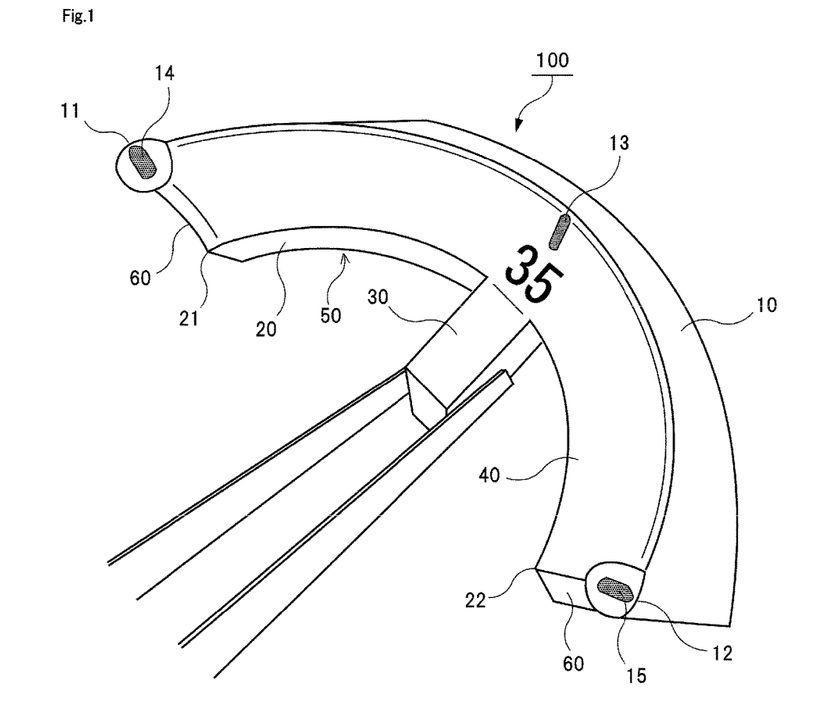
FIG. 1 is a perspective view showing an example of a valve cusp sizer.

FIG. 1 shows an exemplary valve cusp sizer 100 according to the present invention. FIG. 1 schematically shows the valve cusp sizer 100 held by an instrument such as tweezers or a clamp. The valve cusp sizer 100 is a surgical instrument used in an aortic valvuloplasty and the like. A method for using the valve cusp sizer in the aortic valvuloplasty is disclosed in detail in Patent Document 1 and Non-Patent Literature 1. Therefore, an explanation of the aortic valvuloplasty is omitted in the specification of the present application. The disclosure of Patent Document 1 is incorporated into the specification of the present application.

As shown in FIG. 1, the valve cusp sizer 100 has a front surface 10 to be abutted against an organism (specifically an inner wall of blood vessel of an aorta) of a patient. The front surface 10 is formed in an arcuate surface form such that a central part thereof projects toward a side of the organism of the patient. A left contact probe 11 is formed at a left end of the front surface 10, and a right contact probe 12 is formed at a right end of the front surface 10. The left and right contact probes 11, 12 are portions to be abutted against commissure portions positioned at left and right ends of a valve cusp.

Specifically, for example, the valve cusp sizer 100 is inserted into the aorta after excising a valve cusp from an aortic valve composed of three valve cusps, and then the left and right contact probes 11, 12 of the valve cusp sizer 100 are abutted against the commissure portions of valve cusps remained at both positions adjacent to the excised valve cusp. The front surface 10 positioned between the left and right contact probes 11, 12 is provided to have various sizes. Namely, a plurality of types of valve cusp sizers provided for an operation is different in size of the front surface 10 positioned between the left and right contact probes 11, 12. In the example shown in FIG. 1, the length of an arc between the left and right contact probes 11, 12 is about 35 mm (about plus/minus 2 mm is permissible). Thus, the valve cusp sizer 100 is labelled as "35". Note that, an entire length of an arc forming the front surface 10 may be slightly larger than the length of the arc between the left and right contact probe portions 11, 12. Although not shown in the diagrams, a plurality of sizes ranging about from 15 mm to 35 mm is provided for the size (the length of the arc) between the left and right contact probe portions 11, 12. Accordingly, the size of patient's valve cusp can be measured (determined) by selecting the valve cusp sizer 100 having a suitable size, while letting the left and right contact probe portions 11, 12 of the valve cusp sizer 100 abut against the commissure portions of the valve cusps and changing the types of the valve cusp sizers 100.

Figure 2:
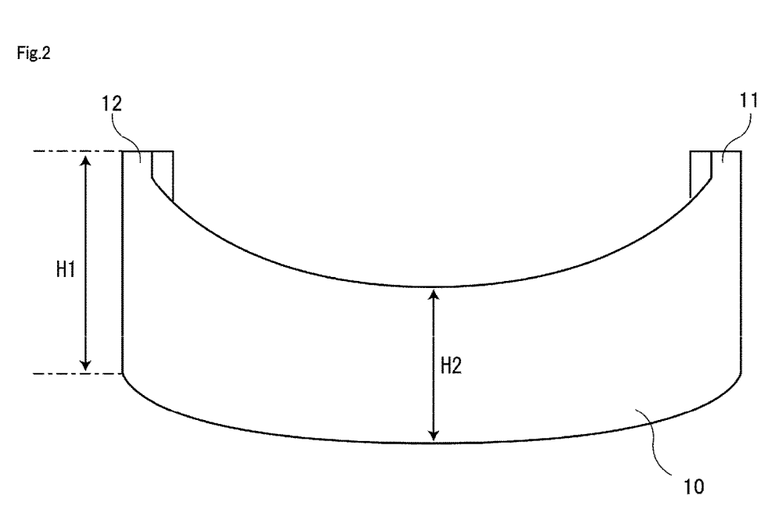
FIG. 2 is a front view showing an example of the valve cusp sizer.

FIG. 2 shows a front view of the valve cusp sizer 100. As shown in FIG. 2, in the front surface 10 of the valve cusp sizer 100, the height H1 of each of left and right ends, at which the contact probe portions 11, 12 are formed respectively, is higher than the height H2 of a central part in a left-right direction. This structure makes it easy to measure the size of the valve cusp with upper ends of the contact probe portions 11, 12 abutting against the commissure portions.

Further, as shown in FIG. 1, a back surface 20 exists on an opposite surface side to the front surface 10. The valve cusp sizer 100 of the present invention is provided with a pinching portion 30 protruding from the back surface 20. Namely, the pinching portion 30 protrudes from the back surface 20 in a direction opposite to a direction in which the front surface 10 exists. As shown in FIG. 1, it is preferable that the pinching portion 30 is positioned on a center line of the back surface 20 in the left-right direction.

The pinching portion 30 is a part to be held by an operator via a surgical instrument such as the clamp or the tweezers. Thus, the pinching portion 30 may have a width (thickness), a height, and a length that can be held by the surgical instrument. It is preferable for the pinching portion 30 that at least surfaces (left and right side surfaces) to be contacted with the surgical instrument are flat surfaces. Basically, it is preferable that the pinching portion 30 is formed in a cuboid shape as shown in FIG. 1, although the shape of the pinching portion 30 is not limited thereto. The pinching portion 30 may be formed in another shape, although an illustration thereof is omitted.

In the example of the valve cusp sizer 100 shown in FIG. 1, the valve cusp sizer 100 has a certain thickness between the front surface 10 and the back surface 20. Therefore, the valve cusp sizer 100 has an upper surface 40, a lower surface 50, and side surfaces 60 each connecting the front surface 10 and the back surface 20. The valve cusp sizer 100 of the present invention, however, may have such a structure that the thickness between the front surface 10 and the back surface 20 is extremely thin and the illustrated upper surface 40, lower surface 50, and side surfaces 60 cannot be identified.

As shown in FIG. 1, the back surface 20 of the valve cusp sizer 100 is formed in a shape projecting in the same direction as that of the front surface 10. Namely, the back surface 20 is formed in a shape recessed toward a side of the front surface 10. For example, the back surface 20 is preferably formed in an arcuate surface form similar to the front surface 10. Further, the back surface 20 and the front surface 10 may be parallel with each other. The back surface 20 may be formed in a polygonal form without being limited to the arcuate surface form. Moreover, even if the back surface 20 is a surface non-parallel to the front surface 10, there are no problems in particular.

Figure 3:
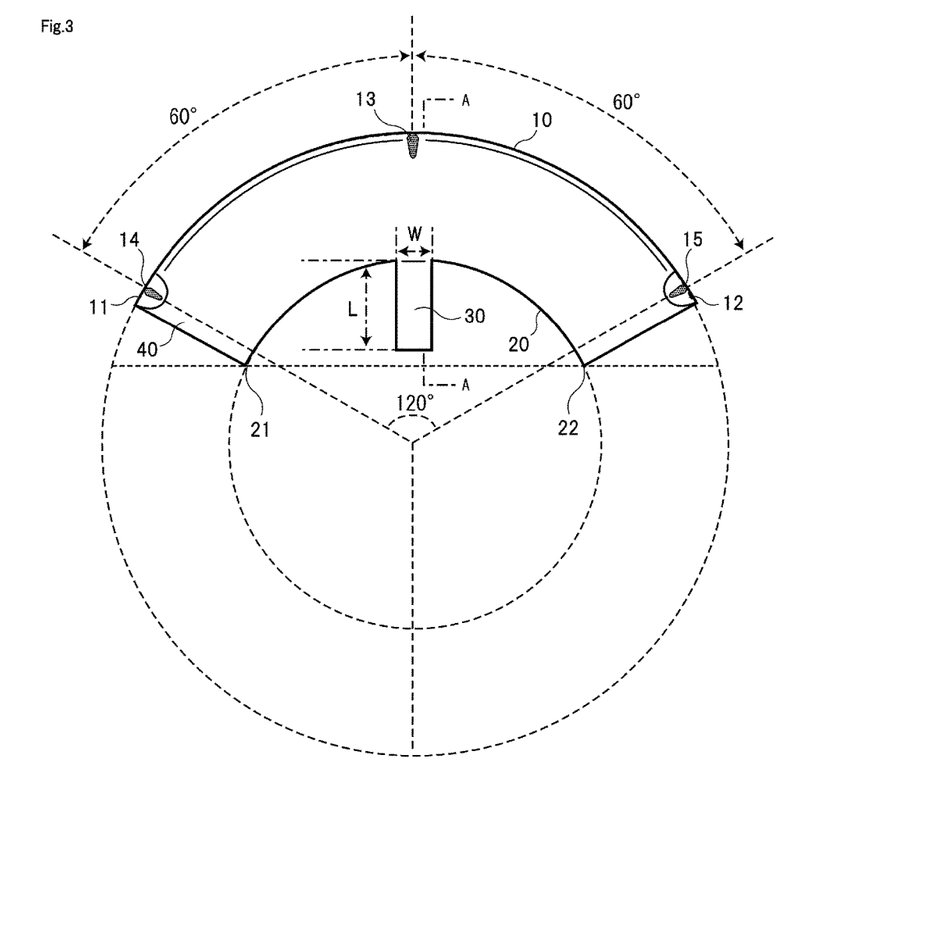
FIG. 3 is a plan view schematically showing the valve cusp sizer.

FIG. 3 schematically shows a plan view viewing the valve cusp sizer 100 from a side of the upper surface 40. In FIG. 3, additional lines to design the valve cusp sizer 100 is shown by dotted lines. As shown in FIG. 3, a basic form of the valve cusp sizer 100 is a fan shape (partial column) cut at an angle confirming to the central angle for the commissure portions of the aortic valve. In the illustrated example, it is assumed that the aortic valve consists of three valve cusps and the central angles for the three commissure portions of the aortic valve are the same 120 degrees. As shown in FIG. 3, the front surface 10 of the valve cusp sizer 100 is an arc form. The length of an arc between the left and right contact probe portions 11, 12 provided on the front surface 10 of the valve cusp sizer 100 is the length conforming to the central angle for the commissure portions. That is, in the example shown in FIG. 3, the arc between the left and right contact probe portions 11, 12 has the length conforming to the central angle of 120 degrees.

Note that, there is a case that the aortic valve consists of two valve cusps, although an illustration thereof is omitted. In this case, the number of the commissure portions of the aortic valve is two. If this case is assumed, the arc of the front surface 10 may be a form conforming to the central angle of 180 degrees.

Further, as shown in FIG. 3, a center index 13, a left index 14, and a right index 15 are preferably formed on the upper surface 40 of the valve cusp sizer 100. The center index 13 is formed at a center in the left-right direction. The left index 14 and the right index 15 are formed in the left contact probe portion 11 and the right contact probe portion 12 respectively on a side of the upper surface 40. In the example shown in FIG. 3, the center index 13 and the left index 14 are provided at an interval conforming to 60 degrees, and the center index 13 and the right index 15 are similarly provided at the interval conforming to 60 degrees. Each of the indexes 13, 14, 15 serves as an index to be observed by an operator's sight, when the size of the cut valve cusp is measured by using the valve cusp sizer 100. Each of the indexes 13, 14, 15 makes it easy for the operator to position the front surface 10 and the left and right contact probe portions 11, 12 of the valve cusp sizer 100.

In FIG. 3, left and right back ends of the back surface 20 formed in the arcuate surface form are indicated by characters 21, 22. In this case, the pinching portion 30 protruding from the back surface 20 is preferably formed in such a length that the pinching portion 30 does not protrude beyond the left back end 21 and the right back end 22 of the back surface 20. In FIG. 3, the left back end 21 and the right back end 22 of the back surface 20 are linked by a virtual line. In this case, the pinching portion 30 has such a length that the pinching portion 30 does not exceed the virtual line linking the left back end 21 and the right back end 22. By forming the pinching portion 30 as described above, the pinching portion 30 can be placed inside a recess formed by the back surface 20. Therefore, it is possible to prevent the pinching portion 30 from interfering an insertion of the valve cusp sizer 100 into the aorta. The length L of the pinching portion 30 is preferably at least not less than 5 mm or not less than 10 mm, while satisfying a condition that the pinching portion 30 does not protrude beyond the left and right back ends 21, 22 of the back surface 20. If the length L of the pinching portion 30 is too short, it is difficult to pinch the pinching portion 30 by the clamp or tweezers. However, if the length L of the pinching portion 30 is not less than 5 mm, the pinching portion 30 can be appropriately pinched by the clamp or the like.

In FIG. 3, the width of the pinching portion 30 is indicated by a character W. The width W of the pinching portion 30 may be determined so that the pinching portion 30 can be pinched easily by the clamp or tweezers. For example, the width W of the pinching portion 30 may be 3 mm to 20 mm, 4 mm to 15 mm, or 5 mm to 10 mm.

Figure 4:
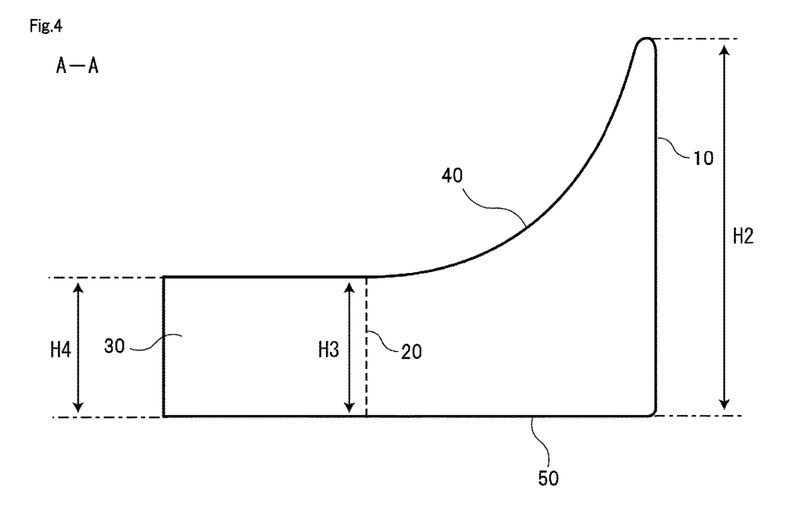
FIG. 4 is a cross sectional view on line A-A shown in FIG. 2.

FIG. 4 shows an outline of a cross section on a line A-A shown in FIG. 3. Namely, FIG. 4 is a cross sectional view of the valve cusp sizer 100 at a part formed with the pinching portion 30. As shown in FIG. 4, when comparing the height H2 at the central portion of the front surface 10 with the height H3 of the back surface 20, the height H3 of the back surface 20 is shorter than the height H2 at the central portion of the front surface 10 (H3<H2). For example, the height H3 of the back surface 20 is preferably about 20% to 80%, or 30% to 50% of the height H2 at the central portion of the front surface 10. Further, as shown in FIG. 3, the front surface 10 and the back surface 20 preferably stand up to be parallel surfaces each other.

Since the height H3 of the back surface 20 is shorter than the height H2 of the front surface 10 as described above, the upper surface 40 connecting the front surface 10 and the back surface 20 is inclined. As shown in FIG. 4, the upper surface 40 is preferably formed to be a gradually curved surface so that the cross section thereof is a curved line. The upper surface 40, however, may be a flat surface so that the cross section thereof is a straight line. On the other hand, the lower surface 50 connecting the front surface 10 and the back surface 20 is formed to be a flat surface so that the cross section thereof is a straight line. As the lower surface 50 is the flat surface as described above, it is easy to allow the valve cusp sizer 100 to self-stand.

In the example shown in FIG. 4, the height H3 of the back surface 20 is identical with the height H4 of the pinching portion 30 (H3=H4). The height H4 of the pinching portion 30, however, may be shorter or taller than the height H3 of the back surface 20. When considering easiness of pinching the pinching portion 30, the height H4 of the pinching portion 30 is preferably taller than the height H3 of the back surface 20 (H4>H3).

Subsequently, referring to FIGS. 5 and 6, examples of improved valve cusp sizer 100 will be explained.

Figure 5:
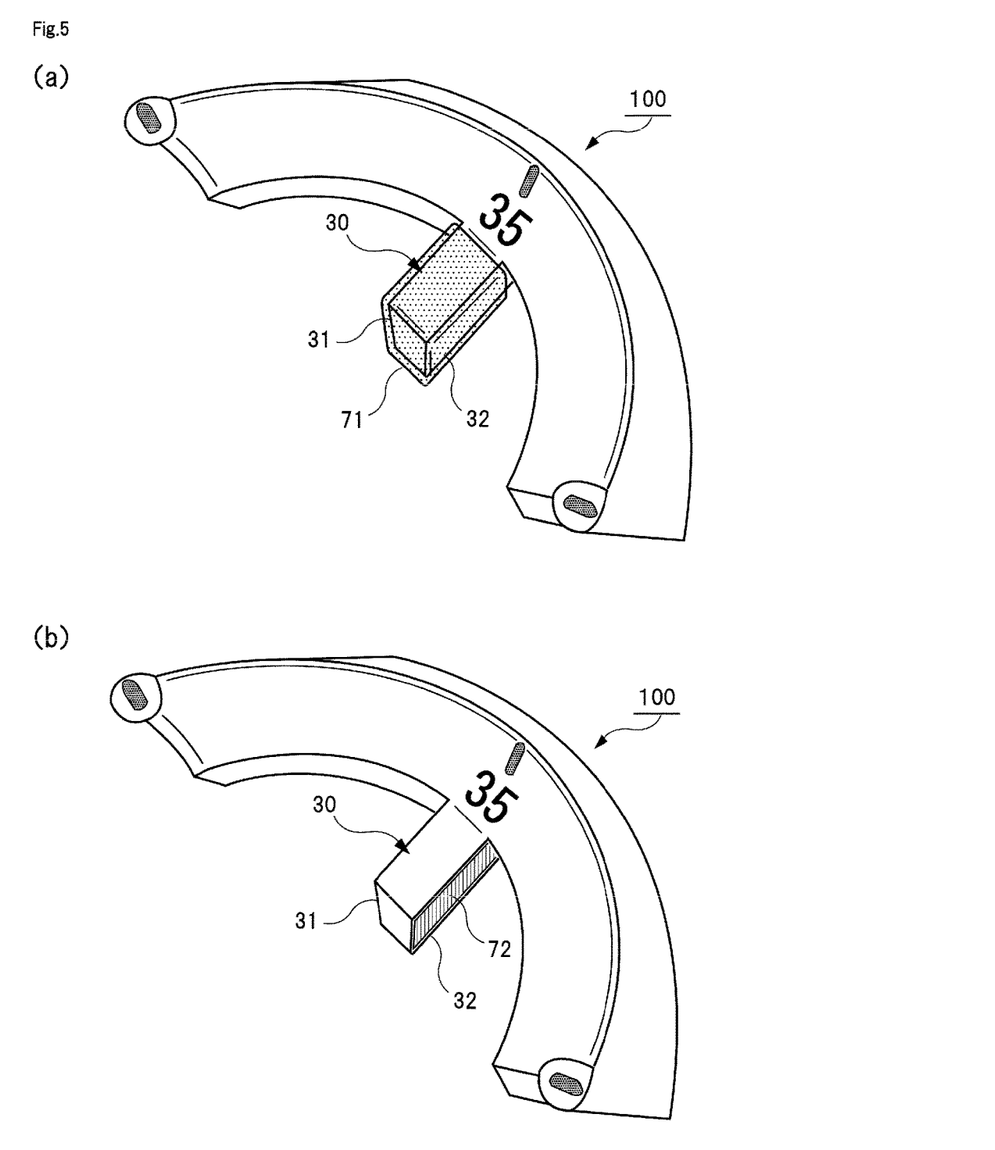
FIGS. 5(a) and 5(b) are perspective views showing examples of other valve cusp sizers.

FIG. 5 shows examples of pinching portion 30 of the valve cusp sizer 100 to which non-slip improvement is applied. In the example shown in FIG. 5(a), a slip stopper 71 is attached to the pinching portion 30. For example, the slip stopper 71 is preferably formed of material having high coefficient of friction such as silicone rubber. Namely, the material forming the slip stopper 71 has preferably higher coefficient of friction than that of material forming a body portion of the valve cusp sizer 100. Publicly known materials can be adopted appropriately as material of the slip stopper. In the example shown in FIG. 5(a), the slip stopper 71 is a cap form having an opening and covers the entirety of the pinching portion 30. However, since the pinching portion 30 is held by pinching the left and right side surfaces 31, 32 thereof, the slip stopper 71 may be positioned at least at the left and right side surfaces 31, 32. For example, the slip stopper 71 can be attached only to the left and right side surfaces 31, 32. The slip stopper 71 can be integrally formed with the pinching portion 30.

In the example shown in FIG. 5(b), a nonslip treatment 72 is applied to the left and right side surfaces 31, 32 of the pinching portion 30. An example of a nonslip treatment 72 may include making the side surfaces 31, 32 of the pinching portion 30 rough surfaces so that the coefficient of friction thereof is enhanced, or forming notches (concave and convex) on the side surfaces 31, 32 of the pinching portion 30 so that tips of the clamp or the tweezers easily fit therein.

The slip stopper 71 or the nonslip treatment 72 shown in FIGS. 5(a) and 5(b) respectively prevents the clamp or the tweezers from slipping when pinching the pinching portion 30, and thereby enhancing safety in the operation in which the valve cusp sizer 100 according to the present invention is used.

Figure 6:
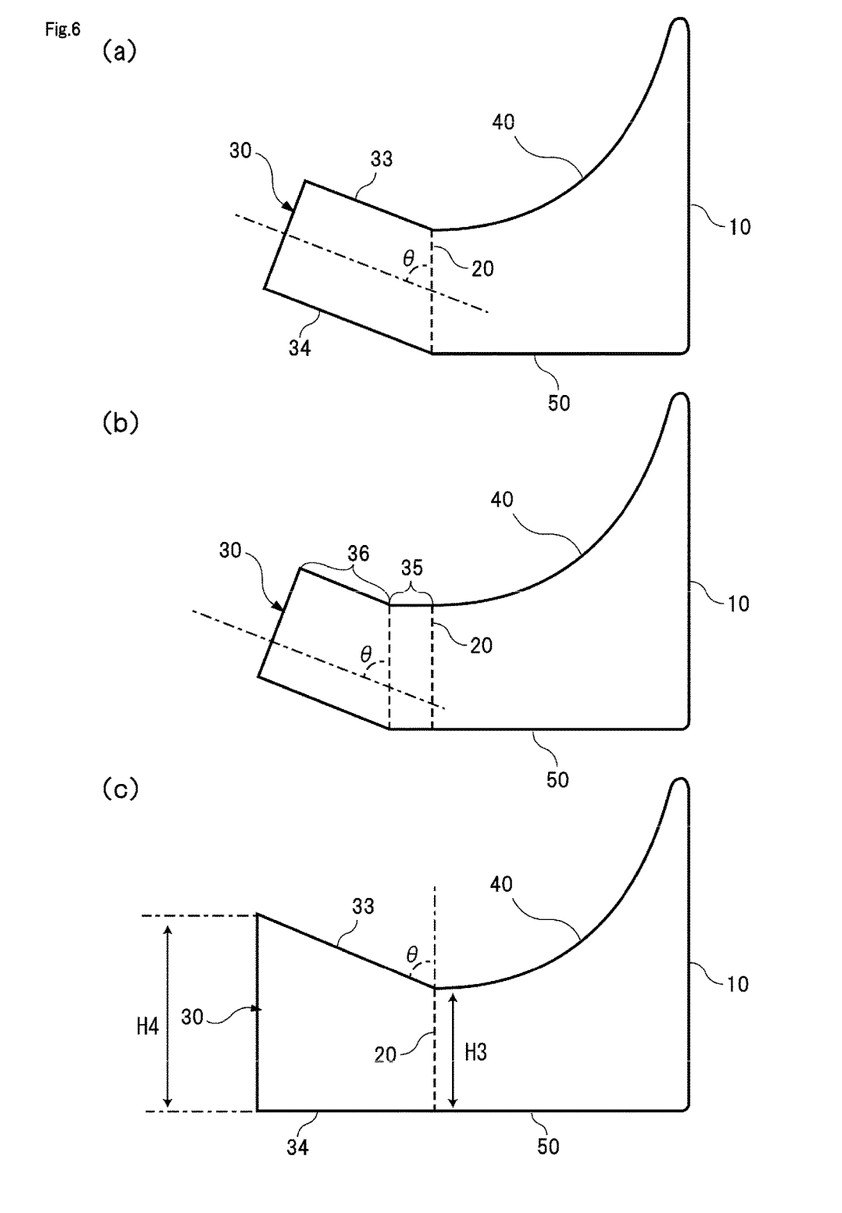
FIGS. 6(a) to 6(c) are cross sectional views showing examples of still other valve cusp sizers.

FIG. 6 shows examples of pinching portion 30 of the valve cusp sizer 100 which are improved to be held easily. In the example shown in FIG. 6(a), the pinching portion 30 is inclined at a predetermined angle θ to the back surface 20 (including a case of standing perpendicular to a placement surface) to stand upwardly. For example, the angle θ may be 0° to 80°, 20° to 60°, or 30° to 45°. In the example shown in FIG. 6(a), the valve cusp sizer 100 has such a structure that the pinching portion 30 rises to a flat surface in a state of the valve cusp sizer 100 being placed on the flat surface. The pinching portion 30 inclined in this manner makes it easy to hold the valve cusp sizer 100 from upside by the clamp or the tweezers. Further, the pinching portion 30 partly inclined upwardly makes it possible to hold the pinching portion 30 so that a grip member of the surgical instrument such as Kelly clamp is parallel to an inclined part of the pinching portion 30 depending on an inclination angle thereof. As a result, the valve cusp sizer can be abutted against the commissure portions at an appropriate angle, thereby reducing a measurement error.

FIG. 6(b) shows an example in which the pinching portion 30 is composed of a non-inclined part 35 and an inclined part 36. The non-inclined part 35 is a part extended from the back surface 20, and the inclined part 36 is a part extended from the non-inclined part 35. The non-inclined part 35 of the pinching portion 30 extends without being inclined to the back surface 20. The inclined part 36 of the pinching portion 30 is inclined at a predetermined angle θ to the back surface 20 (including a case of standing perpendicular to a placement surface) to stand upwardly. For example, the angle θ of the inclined part 36 may be 0° to 80°, 20° to 60°, or 30° to 45°. Since the pinching portion 30 is partly formed by the non-inclined part 35 in this manner, the valve cusp sizer 100 can self-stand stably. Further, since the pinching portion 30 is partly formed by the inclined part 36, it is easy to hold the valve cusp sizer 100 from upside by using the clamp or the tweezers.

FIG. 6(c) shows another example in which an upper surface 33 of the pinching portion 30 is inclined. In the example shown in FIG. 6(c), the upper surface 33 of the pinching portion 30 is an inclined surface so that the height H4 of a back end of the pinching portion 30 is taller than the height H3 of the back surface 20. For example, the height H4 (maximum height) of the pinching portion 30 may be 110% to 200% of the height H3 of the back surface 20. Further, an inclination angle θ of the upper surface 33 of the pinching portion 30 to back surface 20 may be 0° to 80°, 20° to 60°, or 30° to 45°. On the other hand, a lower surface 34 of the pinching portion 30 extends at right angles to the back surface 20. Accordingly, in a state that the valve cusp sizer 100 is placed on a flat surface, the pinching portion 30 is not away from the flat surface. This structure of the pinching portion 30 improves the easiness of pinching the valve cusp sizer 100, and ensures the stable self-standing of the valve cusp sizer 100.

Figure 7:
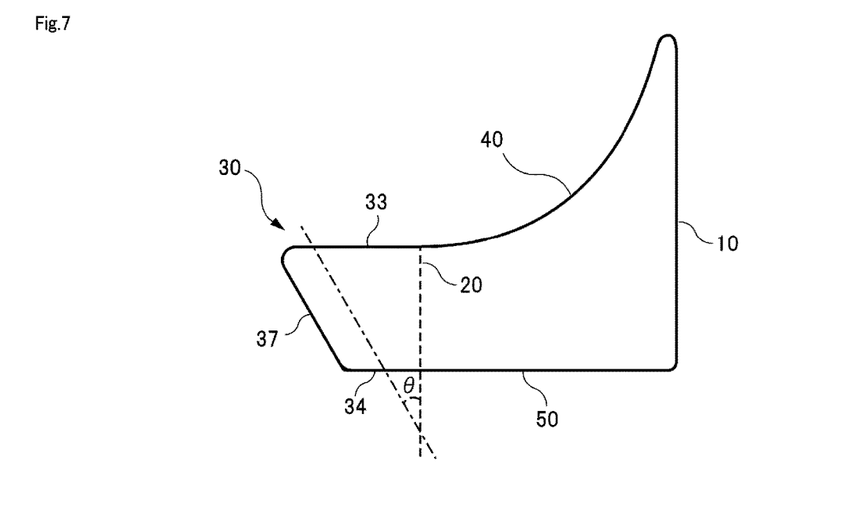
FIG. 7 is cross sectional views showing examples of still other valve cusp size

FIG. 7 shows another example of pinching portion 30 of the valve cusp sizer 100 which are improved to be held easily. In the example shown in FIG. 7, the back surface 37 of the pinching portion 30 is inclined at a predetermined angle θ to the back surface 20 of the valve cusp sizer 100. For example, the angle θ of the back surface 37 of the pinching portion 30 to the back surface 20 may be 10° to 80°, 20° to 60°, or 30° to 45°. The part of pinching portion 30 (the back surface 37) inclined upwardly makes it possible to hold the valve cusp sizer 100 from upside by the clamp or the tweezers so that a grip member of the surgical instrument such as Kelly clamp is parallel to an inclined part of the pinching portion 30 depending on an inclination angle thereof.

In the above specification of the present application, explanation about the embodiments of the present invention has been made while referring to the diagrams to describe the contents of the present invention. The present invention, however, is not limited to the above embodiments, and includes modified or improved embodiments which are obvious for a person skilled in the art based on the described matters in the specification of the present application.

INDUSTORIAL APPLICABILITY

The present invention relates to a valve cusp sizer for measuring the size of a valve cusp composing a cardiac valve. The present invention can be applied suitably to a field of medical instruments.

REFERENCE SIGNS LIST

10: front surface, 11: left contact probe portion, 12: right contact probe portion, 13: center index, 14: left index, 15: right index, 20: back surface, 21: left back end, 22: right back end, 30: pinching portion, 31: left side surface, 32: right side surface, 33: upper surface, 34: lower surface, 35: non-inclined part, 36: inclined part, 37: back surface, 40: upper surface, 50: lower surface, 60: side surface, 71: slip stopper, 72: nonslip treatment, 100: valve cusp sizer

The invention claimed is:

1. A valve cusp sizer for determining a size of a valve cusp conforming to a size of a cardiac valve, comprising:
    a front surface (10) formed in an arcuate surface form to be abutted against an organism;
    a back surface (20) positioned on an opposite surface side of the front surface (10); and
    a pinching portion (30) protruding from the back surface (20) to be pinched by a surgical instrument,
    wherein the front surface (10) is formed in the arcuate surface form in which a central part between left and right ends thereof projects toward a side of the organism.

2. The valve cusp sizer according to claim 1, wherein the front surface (10) includes left and right contact probe portions (11, 12) provided at the left and right ends thereof to contact with left and right commissure portions of the valve cusp.

3. The valve cusp sizer according to claim 1, wherein the back surface (20) is formed in an arcuate surface form projecting toward the same direction as the front surface (10).

4. The valve cusp sizer according to claim 3, wherein the pinching portion (30) is formed to have a length by which the pinching portion does not protrude beyond left and right back ends (21, 22) of the back surface (20).

5. The valve cusp sizer according to claim 1, wherein at least left and right side surfaces (31, 32) of the pinching portion (30) is formed by a slip stopper (71), or a nonslip treatment (72) is applied to at least the left and right side surface (31, 32) of the pinching portion (30).

6. The valve cusp sizer according to claim 1, wherein at least a part of the pinching portion (30) is inclined upwardly.

7. The valve cusp sizer according to claim 2 without a grip member extending upwardly beyond the contact probe portions (11, 12) to be held by hands.

* * * * *